(12) United States Patent
Elsen et al.

(10) Patent No.: US 11,679,070 B2
(45) Date of Patent: Jun. 20, 2023

(54) METHODS FOR TREATING HAIR

(71) Applicant: L'OREAL, Paris (FR)

(72) Inventors: Andrea Elsen, Linden, NJ (US);
Charles Shaw, Madison, NJ (US);
Nghi Van Nguyen, Edison, NJ (US);
Jim Singer, South Orange, NJ (US)

(73) Assignee: L'OREAL, Paris (FR)

( * ) Notice: Subject to any disclaimer, the term of this patent is extended or adjusted under 35 U.S.C. 154(b) by 70 days.

(21) Appl. No.: 15/152,956

(22) Filed: May 12, 2016

(65) Prior Publication Data
US 2017/0326056 A1    Nov. 16, 2017

(51) Int. Cl.
| *A61K 8/49* | (2006.01) |
| *A61K 8/46* | (2006.01) |
| *A61Q 5/04* | (2006.01) |
| *A61Q 5/12* | (2006.01) |

(52) U.S. Cl.
CPC ............ *A61K 8/498* (2013.01); *A61K 8/46* (2013.01); *A61Q 5/04* (2013.01); *A61Q 5/12* (2013.01)

(58) Field of Classification Search
CPC . A61K 8/498; A61K 8/46; A61Q 5/04; A61Q 5/12
See application file for complete search history.

(56) References Cited

U.S. PATENT DOCUMENTS

| 5,223,252 A * | 6/1993 | Kolc ................... A61K 8/447 131/203 |
| 7,615,231 B2 | 11/2009 | Wohlman |
| 9,028,804 B2 | 5/2015 | Nguyen et al. |
| 2007/0092465 A1* | 4/2007 | Wohlman ............... A61K 8/498 424/70.1 |
| 2009/0169502 A1 | 7/2009 | Quadir |
| 2013/0143784 A1 | 6/2013 | Rizk |
| 2013/0272979 A1 | 10/2013 | Nguyen et al. |
| 2015/0034117 A1* | 2/2015 | Pressly .................. A61K 8/447 132/202 |

FOREIGN PATENT DOCUMENTS

| JP | 2013001697 A | 1/2013 |
| WO | WO-2014202234 A1 | 12/2014 |
| WO | WO-2014202235 A1 | 12/2014 |

OTHER PUBLICATIONS

M. Trap and A. Kushelevsky. The Reaction of Glucono Delta Lactone with Proteins. J. Dairy Sci., 68:1985, 2534-2535. (Year: 1985).*
C. R. Robbins and C. H. Kelly. Amino acid composition of human hair. Textile Research Journal, Oct. 1970, 891-896. (Year: 1970).*

* cited by examiner

*Primary Examiner* — Michael P Cohen
(74) *Attorney, Agent, or Firm* — Polsinelli PC

(57) ABSTRACT

The present disclosure relates to methods for treating hair with lactones. The lactones form a covalent thio-ester bond with free thiols groups on chemically treated hair, and thereby impart a "repairing" or "conditioning" effect to the hair, for example, by making the hair more hydrophobic. Typically, after hair has been treated with a composition comprising one or more reducing agents that reduce disulfide bonds of hair to free thiols, a composition comprising one or more lactones is applied to the hair and the one or more lactones react with the free thiols to form a covalent thio-ester bond. Treatment with the lactones prevents reversion of the repaired bonds to their free thiol state after a single application.

15 Claims, No Drawings

METHODS FOR TREATING HAIR

FIELD OF THE DISCLOSURE

The present disclosure relates to methods for treating hair with lactones (such as meadowlactone). The lactones form a covalent thio-ester bond with free thiol groups on chemically treated hair and impart a variety of beneficial effects to the hair.

BACKGROUND

Consumers often look for products and methods for changing the style of their hair. Some consumers seek to convert curly hair into straight hair but others want the opposite, to convert straight hair into curly hair. Hair can be styled with a variety of methods, but not all methods provide permanent and lasting changes to the hair.

Hair treatments for long-lasting (permanent) shaping usually involve the use of chemicals. A chemical treatment for permanently curling hair, commonly referred to as a "perm" or a "permanent," involves the use of chemicals to break and reform the cross-linking bonds of the hair structure. A fiber of human hair comprises three main morphological components: the cuticle, the cortex, and the cell membrane complex (which itself is comprised of a protein matrix of keratin peptide chains, such as cysteine). These peptide chains are linked to each other by disulfide bonds. The natural shape and structural integrity of human hair depends, in part, on the orientation of the disulfide bonds which link the protein chains. Alteration of the disulfide bonds is therefore usually necessary to permanently change the shape of hair.

It is known that certain hair treatments such as dyes, discoloration, perms, straightening the hair can break and cause damage to the hair, including loss of some of its constituents present at the natural state, especially fatty acids such as 18-methyl eicosanoic acid ("18-MEA"), also described as one of the lipids in hair. Natural lipids on the hair coat the cuticle surface of hair and provide hydrophobicity to the hair. As such, chemical treatment or environmental factors can cause the removal of 18-MEA from the surface of the hair, resulting in damaged and sensitized hair.

For example, when chemically treating hair for permanent shaping, the hair is typically washed and wrapped around curlers and a chemical composition or "reagent" is applied. The reagent softens the inner structure of the hair by breaking some of the cross-links within and between the protein chains of the hair (by breaking the disulfide bonds). The hair swells, stretches, and softens around the curlers. After the disulfide bonds have been broken and the hair shape changed, a neutralizer (usually an oxidizing reagent) is applied to the hair to reconnect the disulfide bonds so that the hair maintains the new shape. A similar chemical process can be used to chemically straighten or "relax" hair. This process makes use of the same chemical compositions but the hair is held straight during treatment rather than wrapped around curlers.

The chemical processes involved in permanently shaping hair that change the structure of the hair fibers can damage the hair (in a sense, the breaking of the disulfide bonds is itself damage to the hair). Consumers complain that their hair feels dry and become brittle after chemical treatments, especially after multiple chemical treatments. In addition, the damaged fiber of the hair presents an electrostatic nature, making it difficult to manage the hair, especially during combing or brushing. In addition, the damaged fiber presents a more hydrophilic character, making it very sensitive to water: the fiber tends to swell and/or become frizzy when in contact with ambient moisture, and making it difficult to achieve, in these conditions, good hairstyle hold. Thus, consumers often sacrifice hair quality in terms of softness and shine, in exchange for changes in hair shape with chemical treatments.

SUMMARY OF THE DISCLOSURE

The present disclosure relates to methods for treating hair with lactones (such as meadowlactone) to form covalent thio-ester bonds with free thiol groups on the hair. The covalent attachment of these compounds imparts a "repairing" or "conditioning" effect to the hair by improving the hairs' hydrophobicity. The technology described herein can be used to prevent reversion of the repaired bond of the hair to their free thiol state. It can additionally be used for styling applications, for example for permanently waving, curling, or straightening hair.

When hair is treated with certain chemical compositions such as those for permanently shaping the hair (such as reducing agents), the hair becomes damaged and loses hydrophobicity (and can become dry and brittle). The inventors discovered methods for restoring the hydrophobicity lost due to chemical treatments, and thus a method for repairing hair. After chemically treating hair with a reducing agent to reduce disulfide bonds of the hair to free thiols, lactones are applied to the hair and reacted with the free thiols to form covalent thio-ester bonds, as shown in the schematic below, which uses meadowlactone for reaction with the free thiols.

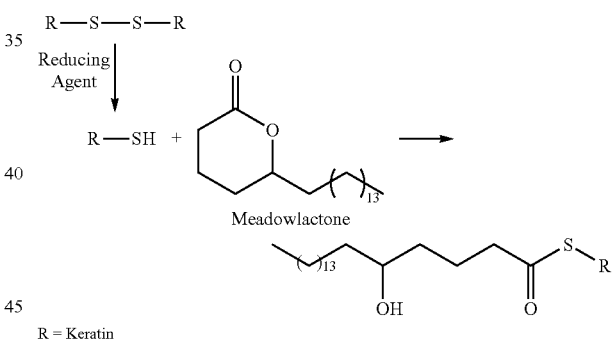

R = Keratin

In some instances, the present disclosure relates to methods for treating hair having two or more free thiol groups, the method comprising applying to the hair a composition comprising one or more lactones in an effective amount to covalently bind the free thiol groups. The lactones and the free thiol groups form a thio-ester bond. Furthermore, methods for treating hair, as disclosed herein, may comprise: (a) applying to the hair a composition comprising one or more reducing agents that reduces disulfide bonds of the hair to free thiols; and (b) applying a composition comprising one or more lactones to the treated hair and reacting the one or more lactones with the free thiols to form covalent thio-ester bonds.

Without being bound to any one theory, the inventors believe that the reaction of a lactone with free thiols on hair that has been treated with one or more reducing agents results in the formation of a complex containing thio-ester bonds, with said complex being similar to or "mimicking" the natural 18-MEA lipids of the hair and thereby imparting hydrophobicity to the hair. Thus, the quality of damaged and/or chemically treated hair can be improved. The increased/improved hydrophobicity of the hair can also contribute to the styling hold on the hair as exhibited by better and/or longer lasting curl retention, even at high humidity conditions. This increased/improved hydrophobicity can also be observed even after shampooing or washing the hair.

The composition comprising the one or more reducing agents (reducing composition) can include one or more of a variety of different reducing agents known in the art. Examples of thiol reducing agents that may be used include, for example, cysteine or a derivative of cysteine, cysteamine or a derivative of cysteamine, thiolactic acid or an ester of thiolactic acid, thioglycolic acid or an ester of thioglycolic acid, and thioglycerol. In some cases, the reducing agent is a glyceryl or glycol monothioglycolate, diammonium dithiodiglycolate, or ammonium thioglycolate.

Hair is treated with a composition comprising the one or more reducing agents for a sufficient amount of time to reduce disulfide bonds of the hair to free thiols, for example, for about 1 to about 30 minutes at a temperature of about 20 to about 45° C. The total amount of the one or more reducing agents in the composition may be, for example, about 0.5 to about 20 wt. %, based on the total weight of the reducing composition. The reducing composition may optionally be rinsed or washed from hair after treatment.

Hair is treated with a composition comprising one or more lactones for a sufficient amount of time for the lactones to react with the free thiols to form covalent thio-ester bonds, for example, for about 1 to about 30 minutes at a temperature of about 20 to about 45° C. The total amount of the one or more lactones in the composition may be, for example, about 0.1 to about 100 wt. %, based on the total weight of the lactone comprising composition.

The instant disclosure also relates to kits. The kits typically include: (a) a composition comprising one or more reducing agents that reduce disulfide bonds of hair to free thiols; and separately (b) a composition comprising one or more lactones that react with free thiols to form a covalent thio-ester bond.

DETAILED DESCRIPTION OF THE DISCLOSURE

The instant disclosure relates to methods for treating hair having two or more free thiol groups, the method comprising applying to the hair a composition comprising one or more lactones in an effective amount to covalently bind the free thiol groups. The lactones and the free thiol groups form a thio-ester bond. This results in a "repairing" or "conditioning" effect imparted to the hair, for example, by making the hair more hydrophobic. The lactones may be substituted by one, two, three, or more hydrophobic fatty moieties.

Improved methods of styling hair, for example, permanent hair waving, hair curling, and hair straightening are also provided. The lactone-containing compositions can be applied one time for a long-lasting effect to hair, or can be applied repeatedly, for example, each time the hair is washed, or daily, once-weekly, twice-weekly, biweekly, once-monthly, every other month, or at less frequent intervals. In some instances the methods described herein relate to permanently shaping hair with chemical treatments and to repairing the chemically treated hair. The disclosure also relates to improving curl retention of hair, preventing frizz of hair, an/or conditioning hair.

The methods described herein may comprise: (a) applying to the hair a composition comprising one or more reducing agents that reduce disulfide bonds of hair to free thiols; and (b) applying a composition comprising one or more lactones to the treated hair and reacting the one or more lactones with the free thiols to form a covalent thio-ester bonds.

The composition comprising the one or more reducing agents can include one or more of a variety of different reducing agents known in the art. The one or more reducing agent may be, for example, an alkali metal sulphite, an alkali metal bisulphites, an alkaline-earth metal sulphite, an alkaline-earth metal bisulphite, an ammonium sulphite, and an ammonium bisulphite, and/or a thiol. Examples of thiol reducing agents that may be used include, for example, cysteine or a derivative of cysteine, cysteamine or a derivative of cysteamine, thiolactic acid or an ester of thiolactic acid, thioclycolic acid or an ester of thioglycolic acid, and thioglycerol. In some cases, the reducing agent is a glyceryl or glycol monothioglycolate, diammonium dithiodiglycolate, or ammonium thioglycolate.

Hair is treated with a composition comprising the one or more reducing agents for a sufficient amount of time to reduce disulfide bonds of the hair to free thiols, for example, for about 1 to about 30 minutes at a temperature of about 20 to about 45° C. In some cases, depending on factors such as the type of reducing agent, concentration of the reducing agent, the type of hair to be treated, etc., the reducing composition may remain on the hair longer or shorter than what is typical in the art, in order to reduce a sufficient number of disulfide bonds of the hair to free thiols. In some cases, the composition comprising the one or more reducing agents may remain on the hair for about 1, 2, 3, 4, 5, or 10 minutes to about 15, 20, 25, 30, 35, 40, 45, or 60 minutes, at a temperature of 20 to 45° C.

The total amount of the one or more reducing agents in the composition may be, for example, about 0.5 to about 20 wt. %, based on the total weight of the reducing composition. The concentration of the one or more reducing agent(s) can depend on the type of reducing agent(s) used, the type of hair to be treated, and the desired results. In some cases, the total amount of the one or more reducing agents in the composition is from about 0.1, 0.5, 1, 2, 3, 4, or 5 wt. % to about 10, 15, 20, 25, 30, 35 or 40 wt. %.

After treating the hair with the reducing composition, the hair can optionally be rinsed to remove the reducing compositions. Typically, water is used to rinse the hair. Rinsing is carried out for a sufficient amount of time to remove most, if not all, of the reducing composition (e.g., at least 90, 95, 96, 97, 98, or 99% of the reducing composition) prior to treatment with a lactone. For example, the hair may be rinsed for about 1, 2, or 3 minutes to about 4, 5, or 10 minutes.

The one or more lactones may be, for example, lactones that are substituted with one, two, three, or more hydrophobic fatty moieties. For example, the hydrophobic fatty moiety may be a $C_5$-$C_{30}$, a $C_5$-$C_{20}$, a $C_5$-$C_{15}$, or a $C_5$-$C_{10}$ alkyl or alkenyl chain. In some cases, the lactone is one or more compounds of formula (I) below.

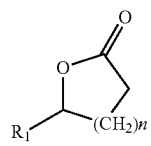

(I)

wherein, $R_1$ is a linear or branched $C_1$-$C_{28}$ alkyl or alkyenyl radical, or a linear or branched $C_1$-$C_{28}$ hydroxyalkyl or hydroxyalkenyl radical; and n is 0, 1, 2, or 3.

Formula (I) above, can be further substituted with one, two, three, or more additional fatty moieties, for example, a fatty moiety such as a $C_5$-$C_{30}$, a $C_5$-$C_{20}$, a $C_5$-$C_{15}$, or a $C_5$-$C_{10}$ alkyl or alkenyl chain.

Non-limiting examples of useful lactones include butyrolactone, gamma-caprolactone, delta-decalactone, gamma-decalatone, meadowfoam delta-lactone (meadowlactone), gamma-nonalactone, gamma-undecalactone. In some cases meadowlactone is used.

The lactone comprising composition is applied to the hair and allowed to remain on the hair for a sufficient amount of time for the one or more lactones to react with the free thiols to form covalent thio-ester bonds, for example, for about 1 to about 30 minutes at a temperature of 20 to 45° C. In some cases, depending on factors such as the type of lactone(s) being used, the concentration of the lactone(s), the type of hair to be treated, etc., the lactone comprising composition may remain on the hair longer than about 30 minutes or shorter than about 1 minute. In some cases, the composition comprising the one or more lactones may remain on the hair from about 1, 2, 3, 4, 5, or 10 minutes to about 15, 20, 25, 30, 35, 40, 45, or 60 minutes at a temperature of 20 to 45° C.

The total amount of the one or more lactones in the lactone comprising composition may be, for example, about 0.1 to about 100 wt. %, based on the total weight of the lactone comprising composition. The composition comprising the one or more lactones may include a cosmetically acceptable solvent or carrier that is compatible with the one or more lactones. For example, the carrier or solvent may comprise water and/or an alcohol. In some cases the lactone comprising composition includes about 0.1 wt. % to about 10 wt. %, about 20 wt. %, about 30 wt. %, about 40 wt. %, about 50 wt. %, about 60 wt. %, about 70 wt. %, about 80 wt. %, about 90 wt. %, or about 100 wt. % of the one or more lactones. In other cases, the lactone comprising composition may include about 50 wt. % to about 70 wt. %, about 80 wt. %, about 90 wt. %, or about 100 wt. % of the one or more lactones. In still other cases, the lactone comprising composition may include at least 50 wt. %, 60 wt. %, 70 wt. % or 80 wt. % to about 100 wt. % of the one or more lactones. The concentration of the one or more lactones depends on the lactone(s) used, the type of hair to be treated, and the desired results.

In some cases, the methods described herein do not require treating the hair with a neutralizing composition (or oxidizing reagent). Treatment with one or more lactones, in many cases, eliminates the need for treatment with a neutralizing composition. Typically, neutralizing composition, include oxidizing agents such as peroxides. However, in some cases, the hair may be treated with an oxidizing composition after being treated with the composition comprising one or more lactones.

The methods described herein can be used to shape various types of hair into a variety of different forms. For instance, to impart waviness or curl to hair, the hair can be wound on curlers during treatment with the reducing composition and the lactone comprising composition. On the other hand, to straighten hair, the hair can be held straight during treatment with the reducing composition and lactone comprising composition. The methods are useful to treat all types of hair, for example, naturally frizzy hair, naturally straight hair, and naturally curly hair.

The present disclosure also relates to methods for imparting hydrophobicity to hair, for example, chemically treated hair. The methods typically comprise: (a) chemically treating hair with a composition comprising one or more reducing agents that reduce disulfide bonds of hair to free thiols; and (b) applying a composition comprising one or more lactones substituted with a hydrophobic fatty moiety to the treated hair and reacting the one or more lactones with the free thiols to form a covalent thio-ester bond. The methods for imparting hydrophobicity to hair are similar to the methods described above for permanently shaping hair and for repairing chemically treated hair, provided that the lactone provides hydrophobicity to the hair.

Finally, the instant disclosure relates to kits. The kits typically include: (a) a composition comprising one or more reducing agents that reduce disulfide bonds of hair to free thiols; and separately (b) a composition comprising one or more lactones that react with free thiols to form a covalent thio-ester bond. Likewise, the disclosure relates to kits for imparting hydrophobicity to hair.

More exhaustive but non-limiting lists of components useful in the compositions disclosed herein are presented below.

Excipients

The compositions described herein for treating hair may contain one or more cosmetically acceptable excipients. Cosmetically acceptable excipients include, but are not limited to, water, preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

Surfactants

Surfactants are surface-active agents that are able to reduce the surface tension of water and cause the composition to slip across or onto the hair. Surfactants also include detergents and soap. The surfactants may be amphoteric, anionic, or cationic. Suitable surfactants that may be used in the compositions described herein for treating hair include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, ammonium C12-16 alkyl sulfate, ammonium C9-10 perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol mono stearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The surfactants are optionally included in an amount ranging from about 0.1 wt. % to about 25 wt. %, about 0.1 wt. % to about 15 wt. %, or about 1 wt. % to about 10 wt. %, based on the weight of the composition.

Emollients

Emollient refers to a material that protects against wetness or irritation, softens, soothes, coats, lubricates, moisturizes, protects, and/or cleanses the hair. Suitable emollients for use in the compositions disclosed herein include, but are not limited to a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or a combination thereof. More than one emollient may be included in the composition.

The emollient is optionally included in an amount ranging from about 0.1 wt. % to about 25 wt. %, about 0.5% to about 15% wt. %, or about 1 wt. % to about 10 wt. %, based on the total weight of the composition.

Emulsifiers

The compositions described herein for treating hair may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, or polysorbate-80, or combinations thereof. More than one emulsifier may be included in the composition.

The emulsifier is optionally included in an amount ranging from about 0.1 wt. % to about 25 wt. %, about 0.5% to about 15% wt. %, or about 1 wt. % to about 10 wt. %, based on the total weight of the composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.01 wt. % to about 5 wt. %, about 0.15% to about 1 wt. %, or about 1 wt. % to about 3 wt. %, based on the total weight of the composition.

Conditioning Agents

One or more conditioning agents may be included in the composition for treatment to the hair. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent(s) are optionally included in an amount ranging from about 0.1 wt. % to about 10 wt. %, about 0.1 wt. % to about 5 wt. %, or from about 0.3% to about 3%, based on the total weight of the composition.

Viscosity Modifying Agents

The compositions may contain one or more viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

Antioxidants

The composition disclosed herein may contain one or more antioxidants. Examples include, but are not limited to, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

Forms

The compositions described herein for treating hair may be in any suitable physical form. Suitable forms include, but are not limited to low to moderate viscosity liquids, lotions, milks, mousses, sprays, gels, creams, shampoos, conditioners, and the like. Suitable excipients, such as those listed above, are included or excluded from the hair care formulation depending on the form of use of the formulation (e.g., hair spray, cream, conditioner, or shampoo).

i. Spray

The compositions described herein for treating hair may be in the form of a spray. The spray typically includes the composition comprising the one or more lactones and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. Preferably, the spray formulation includes a preservative. In some embodiments, the formulation includes a fragrance. In some cases, the compositions described herein include a surfactant. In some cases, the compositions described herein contain water, fragrance, a preservative, and one or more lactones. In some cases, the compositions described herein contain water, fragrance, a preservative, and one or more lactones. In some cases, the composition comprising one or more lactones contains water, a preservative, fragrance, the one or more lactones, and an anti-static agent. In some cases, the compositions described herein contain water, a preservative, fragrance, the one or more lactones, and a hair conditioning agent. In some cases, the compositions described herein contain water, a preservative, fragrance, the one or more lactones, and a surfactant.

The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

ii. Conditioners

The compositions disclosed herein for treatment of hair may be in the form of a conditioner. The conditioner typically includes the composition comprising the one or more lactones in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

iii. Shampoos

The compositions disclosed herein for treatment of hair may be in the form of a shampoo. The shampoo typically includes the one or more lactones in a suitable carrier. The one or more lactones may be included in any suitable concentration. Typical concentrations of the lactones in the shampoo range from small amounts such as approximately about 0.01% (wt), at least 0.1% (wt), to large amounts, such as up to about 50% (wt).

iv. Creams

The compositions disclosed herein for treatment of hair may be in the form of a cream. The cream typically includes one or more lactones in a suitable carrier. The one or more lactones may be included in any suitable concentration. Typical concentrations of the one or more lactones in the cream range from small amounts such as approximately about 0.01% (wt), at least 0.1% (wt), to large amounts, such as up to about 50% (wt).

Methods of Use

A. Treating Damaged Hair with Free Thiol Groups

In one embodiment, prior to treatment with the composition comprising one or more lactones, the hair has been damaged and the thiol groups in the hair are free thiols. The composition comprising the one or more lactones can be applied to the hair to bind the free thiol groups. Typically, the composition comprising the one or more lactones is applied at least within one week of the hair being damaged, usually within three days, two days, and most typically the same day.

a. Rinse or Wash the Hair

Optionally, the hair may be shampooed and/or conditioned prior to applying the composition comprising one or more lactones. Alternately, the hair may only be rinsed with water prior to application of the composition comprising one or more lactones.

b. Apply the Composition Comprising One or More Lactones

Subsequent to shampooing, conditioning, and/or rinsing the hair, the composition comprising one or more lactones is applied to the hair. Alternately, the hair does not need to be washed or rinsed prior to application of the composition comprising one or more lactones. In this respect, the composition comprising one or more lactones may be applied to dry hair.

The composition comprising one or more lactones may be used as a daily conditioning treatment for hair. Typically, the amount of the composition comprising one or more lactones applied is sufficient to saturate the hair. The composition comprising one or more lactones may be applied to the hair as a single application, or application of the composition comprising one or more lactones may be repeated one or more times. Typically, the amount of the composition comprising one or more lactones applied in each application is sufficient to saturate the hair. The volume of the composition comprising one or more lactones applied to the hair in each application may be about 1 to about 100 mL per person depending on their length and volume of hair. In some cases, application of the composition comprising one or more lactones could be repeated immediately (e.g. within about 10 to 15 seconds) or between about one and five minutes, greater than five minutes, between about five and ten minutes, greater than ten minutes, between about ten and twenty (20) minutes after the first application.

c. Remove the Composition Comprising One or More Lactones from the Hair

In some instances, it may be useful to wash or rinse the hair subsequent to the application of the composition comprising one or more lactones. The hair may be rinsed and subsequently washed immediately (e.g. within 10, 15, 25, 30, 45, 60 seconds (one minute), two minutes, three minutes, four, or five minutes following application) after final application of the composition comprising one or more lactones. Alternatively the hair may be rinsed and washed about within about 30 minutes following application, between about 5 minutes and about 20 minutes, or about 10 minutes after the final application of the composition comprising one or more lactones to the hair, depending on the hair type.

Alternately, the hair does not have to be washed or rinsed subsequent to application of the composition comprising one or more lactones.

The composition comprising one or more lactones covalently binds latent free thiols in the hair. The thiols remain bound for at least one week, preferably for at least one month, or longer following application the composition comprising one or more lactones. The thiols may remain bound for longer periods of time, such as for about two months or more following application of the composition comprising one or more lactones.

B. Chemical Treatment of Hair with a Reducing Agent

In some cases, prior to treatment with the composition comprising one or more lactones, the hair has been subjected to a reducing agent used for waving (also referred to herein as hair perming or permanent waves), curling, and/or straightening of the hair.

a. Apply a Reducing Agent to the Hair

The first step in waving, curling, or straightening hair is breaking the cysteine disulfide bonds to form free thiol moieties. The process for breaking the cysteine disulfide bonds is via application of a reducing agent. The process for applying the reducing agent involves following normal perming or hair straightening procedures that are known to those skilled in the art. For example, to perm a hair, the hair is first washed and set on perm rods of various sizes. Second, a reducing agent, such as thioglycolate reducing solution or lotion, is applied to the hair. The hair is allowed to set for a specified period of time, and then the thioglycolate solution is rinsed from the hair.

The application of hydrogen peroxide, in this process, is optional. In some processes, such as when treating previously chemically treated hair, hydrogen peroxide is generally not used. In other processes, such as when perming virgin hair, hydrogen peroxide may be added. In these cases, hydrogen peroxide is typically added after the composition comprising one or more lactones is rinsed out. Then the hydrogen peroxide is rinsed from the hair prior to adding the one or more lactones. Or the process may be reversed, the composition comprising one or more lactones is applied to the hair after treatment with the reducing agent. After application of the composition comprising one or more lactones, the hair is subsequently treated with an oxidizing composition.

b. Apply a Composition Comprising One or More Lactones

Subsequent to the reducing treatment, the composition comprising one or more lactones is applied to the hair. Although the composition comprising one or more lactones is typically applied on the same day as treatment with the reducing agent, it may be applied later, such as within 1 to 2 weeks following treatment with the reducing agent.

Typically, the amount of the composition comprising one or more lactones applied is sufficient to saturate the hair. The composition comprising one or more lactones is generally rinsed and shampooed from the hair after the desired level of hair waving, curling, or straightening is achieved. In some cases, the composition comprising one or more lactones is rinsed from the hair immediately (e.g. within 10, 15, 25, 30, 45, or 60 seconds following application) following the final application of the composition comprising one or more lactones. Alternatively the hair may be rinsed and washed about within about 30 minutes following application, between about 5 minutes and about 20 minutes, or about 10 minutes after the final application of the composition comprising one or more lactones to the hair, depending on the hair type. The composition comprising one or more lactones can be rinsed from the hair within 10, 15, 25, 30, 45, 60 seconds from the hair after application, and still achieve a desired level of hair waving, curling, or straightening.

The composition comprising one or more lactones may be applied to the hair as a single application, or application of the composition comprising one or more lactones may be repeated one or more times. Typically, the amount of the composition comprising one or more lactones applied in each application is sufficient to saturate the hair. In some cases, the volume of the composition comprising one or more lactones applied to the hair in each application is about 1 to about 10 mL per perm rod. In some instances, application of the composition comprising one or more lactones could be repeated immediately (e.g. within 10 to 15 seconds) or approximately 1, 5, 7.5, 10, 12.5, 15, 17.5, or 20 minutes after the first application. In some cases, the second application is about 7 minutes to about 10 minutes after the first application.

The composition comprising one or more lactones is optionally rinsed from the hair after its application. The hair may be rinsed and washed immediately (e.g. within 10 to 15 seconds following application) after final application of the composition comprising one or more lactones. Alternatively the hair may be rinsed and washed about 10 minutes or later after the final application of the composition comprising one or more lactones, such as about 15 minutes to about 30 minutes, or about 20 minutes after repeated application of the composition comprising one or more lactones to the hair.

The lactones in the composition comprising one or more lactones covalently bind the free thiols in the hair. The thiols remain bound for at least one week, two weeks, three weeks, four weeks, one month, two months or more.

The compositions comprising one or more lactones are generally washed from the individual's hair on the same day as they are applied. In contrast, traditional perms which use only hydrogen peroxide are generally not washed for at least 48 hours following application (washing the hair prior to 48 hours following a traditional permanent treatment may result in significant loss in the amount of curl in the hair and/or cause damage to the hair).

The compositions and methods described herein improve hair quality, such as appearance (e.g., sheen) and feel and decrease hair breakage when the hair is subjected to subsequent treatments, such as coloring.

Implementation of the present disclosure is provided by way of the following examples. The examples serve to illustrate the technology without being limiting in nature.

Example 1

Hair Treatment

Naturally frizzy hair swatches (obtained from IHIP) were rinsed and washed with a standard hair shampoo and towel dried. A commercial reducing composition (containing 3.33% of ammonium thioglycolate) was applied to the hair swatches and allowed to remain on the hair swatches for 25 minutes at room temperature. The hair swatches were then rinsed with water for 5 minutes. After rinsing, the hair swatches were treated with either hydrogen peroxide (a standard neutralization treatment) or with meadowlactone (the inventive process). The hydrogen peroxide and the meadowlactone compositions were allowed to remain on the hair for 20 minutes at room temperature. The swatches were rinsed for 5 minutes and blown dry.

Example 2

Hair Repair Properties

Hydrophobicity of each swatch was measured via contact angle measurements using a Biolin Scientific Contact Angle Tensiometer (Model C204A). A bundle of 30-50 fibers was clamped to create a flat surface. A 3 μL drop of DI H$_2$O was placed on the fiber surface and the contact angle was measured for 10 seconds. The hydrophobicity of the hair swatches was measured before washing (immediately after treatment) and again after the hair swatches were shampooed five times using a standard commercial shampoo. The values reported below are an average of 3 measurements using the contact angle at 10 seconds.

| Neutralization Treatment | Contact Angle (initial) | Contact Angle (after shampooing five times) |
|---|---|---|
| None* (Natural Hair) | 105° | 105° |
| Hydrogen Peroxide (standard treatment) | 60° | <60° |
| Meadow Lactone (inventive treatment) | 90° | 85° |

*The hair was not treated with a reducing composition nor was it treated with hydrogen peroxide or meadowlactone (it was completely free of any treatments).

The hair swatches treated with meadowlactone exhibited a much higher contact angle than the hair treated with hydrogen peroxide. The higher contact angle represents higher hydrophobicity. The hydrophobicity (the contact angle) of the hair swatches treated with meadowlactone was more similar to that of natural hair than the hair swatches treated with hydrogen peroxide, even after being shampooed 5 times.

Example 3

Curl Retention Properties

Naturally frizzy hair swatches (obtained from IHIP) were rinsed and washed with a standard hair shampoo and towel dried. The hair swatches were then wound on a spiral rod and treated with a commercial reducing composition (containing 3.33% of ammonium thioglycolate) for 25 minutes at room temperature. The hair swatches were then rinsed with water for 5 minutes (while remaining on the spiral rods) and subsequently treated with hydrogen peroxide (a standard neutralization treatment) or with meadowlactone (the inventive process). The hair swatches were removed from the spiral rods and placed in a humidity chamber (80% RH) at 25° C. for 24 hours. The percentage of curl retention was calculated using the formula below.

$$\% \text{ Curl Retention} = \frac{(Lo - Lt)}{(Lo - Li)} * 100$$

Lo=Original hair length (fully extended hair length)
Li=Initial hair length (length of hair before humidity exposure)
Lt=Length of hair after 24 hour humidity exposure The results are presented in the table below and graphically shown in Figure 1.

| Neutralization Treatment | % Curl Retention (24 hours) |
|---|---|
| None * (Natural Hair) | 58.44% |
| Hydrogen Peroxide (standard treatment) | 49.30% |
| Meadow Lactone (inventive treatment) | 70.59% |

* The hair was not treated with a reducing composition nor was it treated with hydrogen peroxide or meadowlactone (it was completely free of any treatments).

The hair swatches treated with meadowlactone showed a significant increase in curl retention compared to untreated hair and to hair treated with hydrogen peroxide.

Example 4

Contact Angle Measurements

Hair swatches were treated with compositions comprising various concentrations of meadowlactone (0.50 wt. % and 60 wt. %) and the contact angle measured in triplicate. The measurements are presented in the table below. The compositions contained solvent (ethanol) and meadowlactone, in the designated concentrations. The hair swatches were first treated with a commercial perm treatment (a reducing solution). Immediately after rinsing the commercial perm treatment from the hair swatches, the compositions comprising meadowlactone were applied to the hair swatches. The contact angles were immediately measured after treatment with the compositions comprising meadowlactone and again measured after the hair swatches were shampooed five times. The results are presented in the table below.

|  |  | Immediately after Treatment | After Shampooing 5 times |
|---|---|---|---|
| 0.50 wt. % | M1 | 104.5 | 89.1 |
|  | M2 | 99.7 | 123.2 |
|  | M3 | 119.5 | 113.1 |
|  | Av. | 107.9 | 108.5 |
|  | Dev | 10.3 | 17.5 |

|  |  | Immediately after Treatment | After Shampooing 5 times |
|---|---|---|---|
| 60.00 wt. % | M1 | 109.1 | 64.4 |
|  | M2 | 99.1 | 86.5 |
|  | M3 | 102.3 | 71.7 |
|  | Av. | 103.5 | 74.17 |
|  | Dev | 5.1 | 11.2 |

The hair swatches treated with meadowlactone exhibited a high contact angle. A high contact angle represents hydrophobicity. The hydrophobicity (the contact angle) of the hair swatches treated with meadowlactone is similar to that of natural hair, even after being shampooed 5 times.

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term, regardless of whether the term "about" is specifically set forth (or is absent) in conjunction with any particular value in the specification.

When referring to "compositions described herein," all types of compositions are intended unless specifically described otherwise. The "compositions disclosed herein" include the compositions comprising one or more reducing agent, the composition comprising one or more lactones, and to oxidizing compositions.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for treating hair comprising:
   (a) applying to the hair a reducing composition comprising one or more reducing agents that reduces disulfide bonds of the hair to free thiols; and
   (b) subsequently applying a composition comprising one or more lactones to the hair and covalently bonding only the one or more lactones with the free thiols, wherein the one or more lactones form a covalent thio-ester bond, thereby increasing the hydrophobicity of the hair.

2. The method of claim 1, wherein the one or more reducing agents of (a) are selected from the group consisting of an alkali metal sulphite, an alkali metal bisulphites, an alkaline-earth metal sulphite, an alkaline-earth metal bisulphite, an ammonium sulphite, and an ammonium bisulphite, and a thiol.

3. The method of claim 2, wherein the one or more reducing agents of (a) comprises a thiol.

4. The method of claim 3, wherein the thiol is selected from the group consisting of cysteine or a derivative of cysteine, cysteamine or a derivative of cysteamine, thiolactic acid or an ester of thiolactic acid, thioglycolic acid or an ester of thioglycolic acid, and thioglycerol.

5. The method of claim 3, wherein the thiol is thioglyceryl, glycol monothioglycolate, diammonium dithiodiglycolate, or ammonium thioglycolate.

6. The method of claim 1, wherein the total amount of the one or more reducing agents in the composition of (a) is about 0.5 to about 20 wt. %, based on the total weight of the composition of (a).

7. The method of claim 1, wherein the one or more lactones of (b) comprises a compound of formula (I)

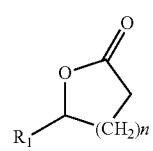

(I)

wherein, $R_1$ is a linear or branched $C_1$-$C_{28}$ alkyl or alkyenyl radical, or a linear or branched $C_1$-$C_{28}$ hydroxyalkyl or hydroxyalkenyl radical; and n is 0, 1, 2, or 3.

8. The method of claim 7, wherein the compound of formula (I) is selected from the group consisting of butyrolactone, gamma-caprolactone, delta-decalactone, gamma-decalatone, meadowfoam delta-lactone (meadowlactone), gamma-nonalactone, gamma-undecalactone.

9. The method of claim 8, wherein the compound of formula (I) is meadowfoam delta-lactone (meadowlactone).

10. The method of claim 1, wherein the composition of (a) is applied to the hair and allowed to remain on the hair for about 1 to about 30 minutes at a temperature of about 20 to about 45° C.

11. The method of claim 1, wherein the method improves curl retention of curled hair.

12. The method of claim 1, wherein the composition comprising one or more lactones of (b) comprises one or more surfactants.

13. The method of claim 12, wherein the method improves curl retention of curled hair.

14. A method for treating hair comprising:
   (a) applying to the hair a reducing composition comprising about 0.5 to about 20 wt. % of one or more reducing agents that reduces disulfide bonds of the hair to free thiols, the one or more reducing agent being selected from the group consisting of thioglyceryl, glycol monothioglycolate, diammonium dithiodiglycolate, ammonium thioglycolate, and a mixture thereof, wherein the reducing composition is allowed to remain on the hair for about 1 to about 30 minutes at a temperature of about 20 to about 45° C.; and
   (b) subsequently applying a composition comprising meadowfoam delta-lactone (meadowlactone) to the hair and covalently bonding only the meadowfoam delta-lactone (meadowlactone) with the free thiols, wherein the meadowfoam delta-lactone (meadowlactone) forms a covalent thio-ester bond, thereby increasing the hydrophobicity of the hair.

15. The method of 14, wherein the composition comprising one or more lactones of (b) comprises one or more surfactants.

\* \* \* \* \*